US006235124B1

(12) United States Patent
Rubin

(10) Patent No.: US 6,235,124 B1
(45) Date of Patent: May 22, 2001

(54) METHOD AND SOLUTION FOR REMOVAL OF MILDEW

(75) Inventor: Lynn J. Rubin, Atlantic Beach, NC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/548,382

(22) Filed: Apr. 10, 2000

(51) Int. Cl.[7] .................................................. B08B 3/02
(52) U.S. Cl. ........................ 134/26; 134/2; 134/22.17; 134/22.19; 134/22.18; 134/29; 134/30; 134/34; 134/42; 510/199; 510/378; 510/421
(58) Field of Search ...................... 510/199, 378, 510/421; 134/2, 22.17, 22.19, 22.18, 26, 29, 30, 34, 42

(56) References Cited

U.S. PATENT DOCUMENTS

| | | |
|---|---|---|
| 4,097,395 | 6/1978 | Posey et al. . |
| 4,164,477 | 8/1979 | Whitley . |
| 4,533,487 | 8/1985 | Jones . |
| 4,975,109 * | 12/1990 | Friedman, Jr. et al. ................. 71/67 |
| 5,000,868 * | 3/1991 | Wittpenn, Jr. et al. ............... 252/106 |
| 5,256,182 * | 10/1993 | Friedman, Jr. et al. .............. 504/124 |
| 5,320,805 * | 6/1994 | Kramer et al. .......................... 422/28 |
| 5,545,349 * | 8/1996 | Kurii et al. ....................... 252/186.38 |
| 5,567,247 * | 10/1996 | Hawes et al. ........................... 134/36 |
| 5,602,090 | 2/1997 | Melikyan et al. . |
| 5,605,578 * | 2/1997 | Hawes et al. ........................... 134/36 |
| 5,783,550 * | 7/1998 | Kuriyama et al. ................... 510/372 |
| 5,959,104 * | 9/1999 | Arbogast et al. ..................... 544/163 |
| 6,159,391 * | 12/2000 | Kobayashi et al. ............. 252/186.38 |

FOREIGN PATENT DOCUMENTS

WO 96/06911 * 3/1996 (WO) .
WO 98/07815 * 2/1998 (WO) .

OTHER PUBLICATIONS

Military Specification for MIL–D–16791G, pp. 1–19, Jan. 1990.*

* cited by examiner

*Primary Examiner*—Sharidan Carrillo
(74) *Attorney, Agent, or Firm*—Mark O. Glut

(57) ABSTRACT

A solution for mildew removal, which includes an aqueous solution of 1–2%(weight by volume) sodium perborate and a non-ionic detergent added as a surfactant. A method for mildew removal, which includes mixing sodium perborate in an aqueous solution wherein the sodium perborate is 1–2% weight by volume, adding a non-ionic detergent to the solution, applying the solution to an infected area, and rinsing the infected area.

3 Claims, No Drawings

METHOD AND SOLUTION FOR REMOVAL OF MILDEW

STATEMENT OF GOVERNMENT INTEREST

The invention described herein may be manufactured and used by or for the Government of the United States of America for governmental purposes without payment of any royalties thereon or therefor.

BACKGROUND

Mildew growth on interior surfaces of aircraft, particularly military aircraft has been a chronic problem, particularly when these aircraft are operated in humid climates. Excess buildup of mildew can cause corrosion as well as operational damage to aircraft. Mildew can also cause accelerated degradation of paint and decals. Mildew buildup is also a health hazard to pilots and maintenance personnel. Buildup of mildew causes unpleasant odors and can be demoralizing to pilots, maintenance personnel and passengers.

Current methods of mildew removal have proven to be extremely time consuming and often inadequate. Solutions that adequately removed mildew in the past have caused accelerated corrosion to the aircraft structural metals as well as to the aircraft. Other solutions, such as ones containing sodium hypochlorite (chlorine bleach), are damaging to the environment and may only bleach the mildew stain and not remove it. Certain solutions require many ingredients, which are difficult, potentially dangerous and time consuming to prepare and use. Other solutions are expensive as well as difficult and dangerous to store.

For the foregoing reasons, there is a need for a new method and solution for mildew removal. Information relevant to attempts to address these problems can be found in U.S. Pat. Nos. 4,097,395, 4,164,477, 4,533,487 and 5,602,090 (None of these patents are admitted to be prior art with respect to the present invention.) However, each of these references suffers from one of the above listed disadvantages.

SUMMARY

The present invention is directed to a chemical compound and method that satisfies the needs enumerated above and below.

The instant invention is directed to a solution for mildew removal which comprises of an aqueous solution of 1–2% (weight by volume) of sodium perborate and a non-ionic detergent added as a surfactant.

The present invention is also directed to a method for mildew removal which comprises of mixing sodium perborate in an aqueous solution, wherein the sodium perborate is 1–2% weight by volume, then adding a non-ionic detergent and applying the solution to an area infected with mildew, and then rinsing the infected area.

It is an object of the present invention to provide a solution and method for mildew removal that is inexpensive, easy to store and environmentally friendly. Sodium perborate is a colorless, free flowing granular chemical that is easy to store and use. The solution decomposes into water, oxygen and sodium borate. It is also non-corrosive to common aircraft structural material.

It is also an object of the invention to provide a solution and method for mildew removal that is non-corrosive to aluminum, steel and aircraft structural materials. The solution may actually inhibit corrosion by passivating metal surfaces and increasing the life of various materials. The solution and method may also possibly delay the growth of mildew on aircraft. The solution may also be used on cars, trucks, trains, ships, buildings or any other object that needs removal of mildew.

It is a further object of the invention to provide a method and solution, which provides mildew cleaning, bleaching, and stain removal. The cleaner also works to enhance removal of common operational oils and soils as well as the removal of mildew.

It is also an object of the present invention to provide a solution that breaks down protein channels within the fungus (mildew), thus eliminating its presence, not just bleaching the stain.

It is also an object of the invention to reduce cleaning time of aircraft. Current methods require significant cleaning time and can cause delays in having the aircraft available for use. The present invention has shown to decrease cleaning time.

These and other features, aspects and advantages of the present invention will become better understood with reference to the following description and appended claims.

DESCRIPTION

The invention is a new method and solution for mildew removal. In the preferred embodiment, the solution for mildew removal comprises of an aqueous solution of 1–2% (weight by volume) sodium perborate (also known as sodium perborate monohydrate) with a non-ionic detergent added as a surfactant. The non-ionic detergent can be mixed into the solution with a ratio of one half (½) ounce of non-ionic detergent per gallon of water. For optimal results the pH range of the solution should be in the range of 9.5 to 10.0 and the temperature of the solution at least 77 degrees Fahrenheit.

The non-ionic detergent can be any detergent conforming to military specification MIL-D-16791 (incorporated herein by reference) or equivalent. The specification requires a detergent to be a liquid, non-ionic surface active agent containing a minimum of 99% active ingredient. The detergent can be the alkyl aryl polyether alcohol (alkyl phenol ether of polyethylene glycol) type where the alkyl group is iso-octyl or isononyl, or the linear alkyl polyether alcohol (alkyl ether of polyethylene glycol) type where the alkyl group is linear primary or secondary alkyl.

The method for mildew removal comprises of the steps of mixing sodium perborate in an aqueous solution wherein the sodium perborate is 1–2% weight by volume, adding a non-ionic detergent to the solution, applying the solution to an mildew infected area, and rinsing the infected area. The rinsing of the infected area can be done by spraying the infected area with pressurized water. The pressure of the water can be in the range of 50 to 80 pounds per square inch (psi). A pressure greater than 80 psi can cause damage to the aircraft, while a pressure less than 50 psi may not be as effective. The solution can have a pH between 9.5 to 10.0. The solution should not have a pH above 10.0 because a pH above 10.0 causes accelerated corrosion on aircraft parts. The preferred ratio of detergent is ½ ounce of non-ionic detergent per gallon of water. As stated above the non-ionic detergent can be any detergent conforming to military specification MIL-D-16791.

To improve performance of the solution and method the solution should be left on the mildew infected area for five to ten minutes and then rinsed. Prior to rinsing, the mildew infected area containing the solution can also be scrubbed with cheesecloth or any type of brush. The temperature of the solution can be from 32 degrees Fahrenheit to 212 degrees Fahrenheit. At temperatures less than 32 degrees part of the solution can freeze; at temperatures higher than 212 degrees part of the solution can boil. The preferred temperature is at least 77 degrees. The warmer the solution the better results, however, if the solution is too warm or hot it may burn the user or cause damage to attached decals.

Although the present invention has been described in considerable detail with reference to certain preferred versions thereof, other versions are possible. Therefore, the spirit and scope of the appended claims should not be limited to the description of the preferred versions contained herein.

What is claimed is:

1. A method for removal of mildew from an aircraft, which comprises;
    (a) preparing an aqueous solution consisting of sodium perborate, and a non-ionic detergent, the non-ionic detergent being an alkyl aryl polyether alcohol, the aqueous solution having a pH in a range from 9.5 to 10.0;
    (c) applying the aqueous solution to a mildew infected area on said aircraft; and
    (d) rinsing the mildew infected area using pressurized water, the pressurized water having a pressure in a range from 50 to 80 psi and a temperature of at least 77 degrees Fahrenheit.

2. The method of claim 1, wherein the aqueous solution is left on the mildew infected area for five to ten minutes before rinsing.

3. The method of claim 2, wherein the mildew infected area containing the aqueous solution is scrubbed prior to rinsing and after applying the aqueous solution.

* * * * *